United States Patent [19]

Jacobs et al.

[11] Patent Number: 5,080,674
[45] Date of Patent: Jan. 14, 1992

[54] ATTACHMENT MECHANISM FOR SECURING AN ADDITIONAL PORTION TO AN IMPLANT

[75] Inventors: Carl H. Jacobs, South Bend; H. Ravindranath Shetty, Warsaw, both of Ind.

[73] Assignee: Zimmer, Inc., Warsaw, Ind.

[21] Appl. No.: 587,489

[22] Filed: Sep. 20, 1990

Related U.S. Application Data

[63] Continuation of Ser. No. 241,747, Sep. 8, 1988, abandoned.

[51] Int. Cl.⁵ .................................. A61F 2/38
[52] U.S. Cl. .................................. 623/20
[58] Field of Search ........................ 623/20, 18

[56] References Cited

U.S. PATENT DOCUMENTS

| | | | |
|---|---|---|---|
| 3,293,106 | 12/1966 | Cocco et al. | 161/112 |
| 3,605,123 | 9/1971 | Hahn | 3/1 |
| 3,906,550 | 9/1975 | Rostoker et al. | 3/1.912 |
| 3,943,576 | 3/1976 | Sivash | 3/1 |
| 4,198,711 | 4/1980 | Zeibig | 623/18 |
| 4,205,400 | 6/1980 | Shen et al. | 3/1.91 |
| 4,479,271 | 10/1984 | Bolesky et al. | 3/1.911 |
| 4,570,271 | 2/1986 | Sump | 623/18 |
| 4,636,219 | 1/1987 | Pratt et al. | 623/22 |
| 4,693,724 | 9/1987 | Rhenter et al. | 623/23 |
| 4,718,915 | 1/1988 | Epinette | 623/23 |
| 4,731,086 | 3/1988 | Whiteside et al. | 623/20 |
| 4,769,039 | 9/1988 | Horber | 623/20 |
| 4,838,891 | 6/1989 | Branemark et al. | 623/20 |
| 4,842,606 | 6/1989 | Kranz et al. | 623/23 |
| 4,883,488 | 11/1989 | Bloebaum et al. | 623/18 X |
| 4,883,492 | 11/1989 | Frey et al. | 623/18 X |
| 4,969,907 | 11/1990 | Koch et al. | 623/20 |

FOREIGN PATENT DOCUMENTS

| | | |
|---|---|---|
| 0218032A1 | 4/1987 | European Pat. Off. |
| WO81/03038 | 10/1981 | PCT Int'l Appl. |
| 0325743A | 2/1930 | United Kingdom |
| 0570735A | 7/1945 | United Kingdom |
| 0572082A | 9/1945 | United Kingdom |
| 2059267A | 4/1981 | United Kingdom |
| 2142544A | 1/1985 | United Kingdom |

*Primary Examiner*—David J. Isabella
*Attorney, Agent, or Firm*—Margaret L. Geringer

[57] ABSTRACT

A prosthetic implant including a base portion and an additional portion which is to be securely attached to the base portion. The additional portion includes at least one post extending therefrom which is adapted to be readily received in a corresponding reverse tapered hole in the base portion. The post is adapted to be mechanically spread out to cause at least a portion of the post to become wider than the opening of the hole, thus resisting subsequent separation of the post from the hole. This secures the additional portion to the base portion of the implant. The post may be a stud-type extension integrally formed with or secured to the additional portion, or the post may be a separate member which is received in a post hole in the additional portion such that the post portion of the separate member extends from the additional portion. The post may be solid or may have a channel therethrough. The additional portion may include a substrate with a porous surface bonded or secured thereto.

17 Claims, 3 Drawing Sheets

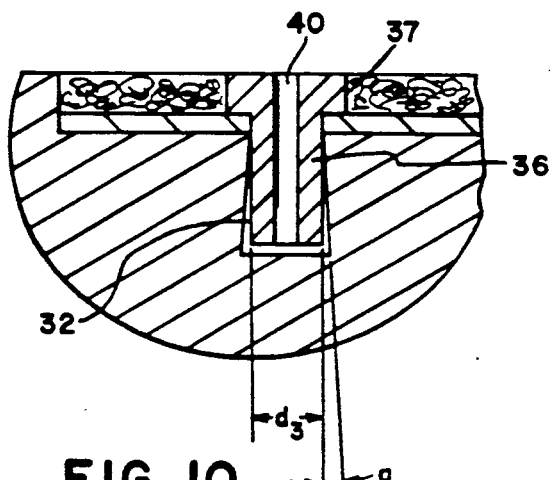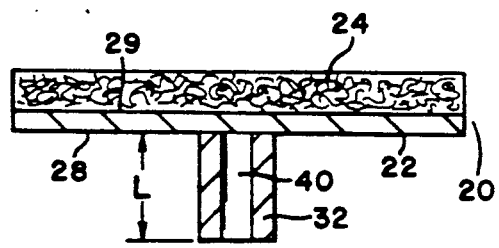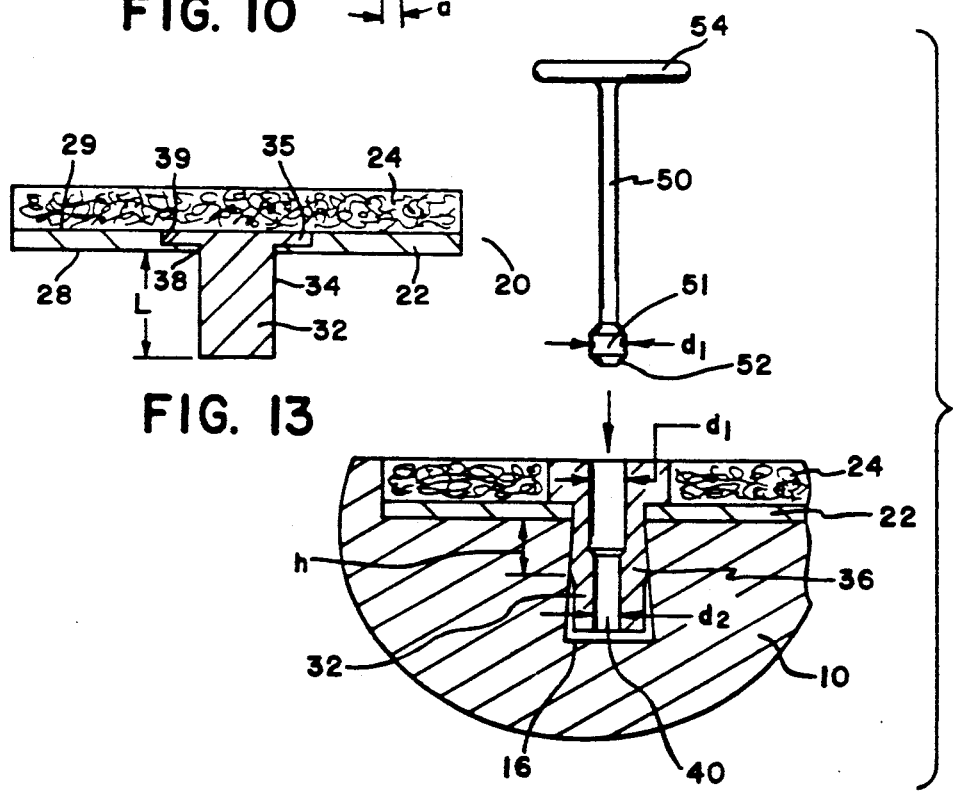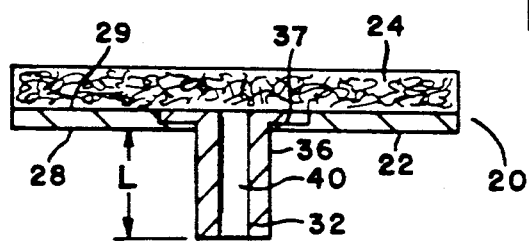

ATTACHMENT MECHANISM FOR SECURING AN ADDITIONAL PORTION TO AN IMPLANT

This application is a continuation of application Ser. No. 07/241,747 filed Sept. 8, 1988 now abandoned.

BACKGROUND OF THE INVENTION

The present invention relates to a prosthetic implant device, and more particularly to such implants which include at least two portions which need to be secured or attached together.

Heretofore, various types of attachment mechanisms have been utilized to secure two portions or layers of implants together.

U.S. Pat. No. 4,205,400 to Shen et al. discloses a polyethylene layer which is presumably molded onto a metallic support member via reverse tapered holes in the metallic member so that the polymeric layer is securely connected to the metallic member.

U.S. Pat. No. 3,906,550 to Rostoker et al. discloses a porous fiber metal structure adapted for attachment to a prosthesis. The fiber metal material is molded directly into the desired shape using dies and punches. The fiber metal is then sintered together to form metallurgical bonds between the fibers.

U.S. Pat. No. 3,605,123 to Hahn discloses a metallic bone implant having a porous metallic surface layer. The porous layer may be secured to the implant by plasma spraying the porous coating thereto or by other suitable means.

U.S. Pat. No. 4,731,086 to Whiteside et al. discloses a shim to increase the effective thickness of a femoral knee. The pegs 18 and 18' on the femoral component may be inserted through openings 26 and 26' in the shim.

U.S. Pat. No. 4,718,915 to Epinette discloses a hip prosthesis which includes two packing pieces attached thereto by a stud with a frustroconical head that engages a dovetail-shaped channel.

U.S. Pat. No. 4,693,724 to Rhenter et al. discloses a femoral hip prosthesis in which the mounting of the neck 17 on the pin 1 has been achieved by means of a setting screw 23.

U.S. Pat. No. 4,636,219 to Pratt et al. discloses a prosthesis including a porous surface comprised of a layered metal mesh structure and a process for fabricating the mesh screen structure for bonding to the prosthesis. The mesh may be bonded to a thin substrate which can then be cut or formed and applied to the body of a prosthesis on a flat surface as in FIG. 3 of Pratt et al. or contoured into specific shapes by processes such as creep forming.

U.S. Pat. No. 4,570,271 to Sump discloses a prosthesis with a porous surface in which the porous coating is preformed directly into the desired shape which corresponds to the preselected surface of the prosthesis. The preform porous coating is then overlaid onto the preselected surface, compressed, and heated to adhere the preform to the prosthesis.

U.S. Pat. No. 4,479,271 to Bolesky et al. discloses a prosthesis including porous surfaces which are either molded and compressed directly into shape or compressed and cut directly into shape. A polyethylene layer is molded onto the intermediate metal reinforcing layer and the porous bottom base layer. The porous layer is metallurgically bonded to the reinforcing layer. The attachment of the polyethylene layer is enhanced by penetration of the polyethylene into the porous material via openings in the reinforcing layer.

U.K. Patent Application GB 2 142 544 A to Medcraft discloses a method of making a surgical implant including diffusion bonding a mesh sheet to a substrate.

U.S. Pat. No. 3,293,106 to Cocco et al. discloses a connection for attaching metal foil to a plastic substrate. The connection includes a support base with at least one recess formed therein and a second flat material positioned on the base and at least one protuberance formed from the second material and extending into the recess at an angle to the horizontal plane of the second material. The innermost end of the protuberance in the recess is apertured. An adhesive is utilized in each cavity/recess which is bonded to the base and extends from the recess through the aperture to cover all exterior surfaces of the protuberance substantially flush to the outer surface of the second material.

OBJECTS AND SUMMARY OF THE INVENTION

A principle object of this invention is to provide an attachment mechanism for securing an additional portion to the base portion of an implant.

Another object of this invention is to provide an attachment mechanism which is particularly suitable for securing materials having dissimilar bonding capabilities, although is not limited thereto.

A further object of the invention is to provide a simple and effective mechanical attachment mechanism.

The present invention provides an attachment mechanism for securing an additional portion to a prosthetic implant. The implant includes a base portion with a receiving surface and an additional portion which is to be securely attached to the receiving surface. The additional portion includes an interfacing surface. At least one hole or cavity is included in either the receiving surface or the interfacing surface and the other of these two surfaces includes at least one corresponding post extending therefrom. The hole includes an opening and an inner wall extending therefrom having a reverse taper such that the hole widens as it extends into the surface that the hole is in. The post is adapted to be received in the hole and is also adapted to be spread out to cause at least a portion of the post to become wider than the opening of the hole, thus resisting subsequent separation of the post from the hole to secure the additional portion to the base portion of the implant.

BRIEF DESCRIPTION OF THE DRAWINGS

These features and objects of the invention, as well as others, will become apparent to those skilled in the art by referring to the accompanying drawings:

FIG. 10 is a further alternate embodiment of a partial cross-sectional view taken along lines 6—6 of FIG. 5;

FIG. 11 is a partial cross-sectional view of the embodiment of FIG. 10 after the peg has been spread out by the plunger;

FIG. 12 is an alternate embodiment of the additional portion of FIG. 3; and

FIGS. 13 and 14 are further alternate embodiments of the additional portion.

DETAILED DESCRIPTION OF THE INVENTION

FIGS. 1-14 illustrate several particularly advantageous embodiments of a prosthetic implant according to the present invention. The invention will be described with reference to a femoral knee implant component 1 and is particularly suitable as such. However, it is understood that the principles of the invention may be utilized with other types of implants.

Figure 1:
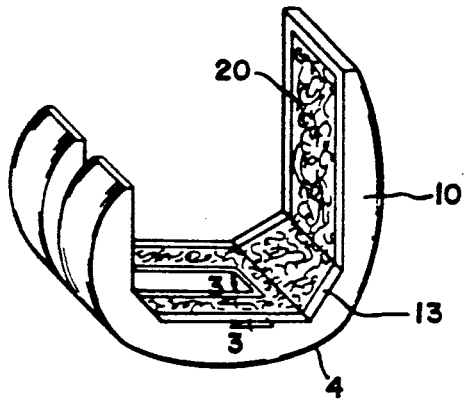
FIG. 1 is a perspective view of a femoral knee implant component in accordance with the present invention.
Figure 2:
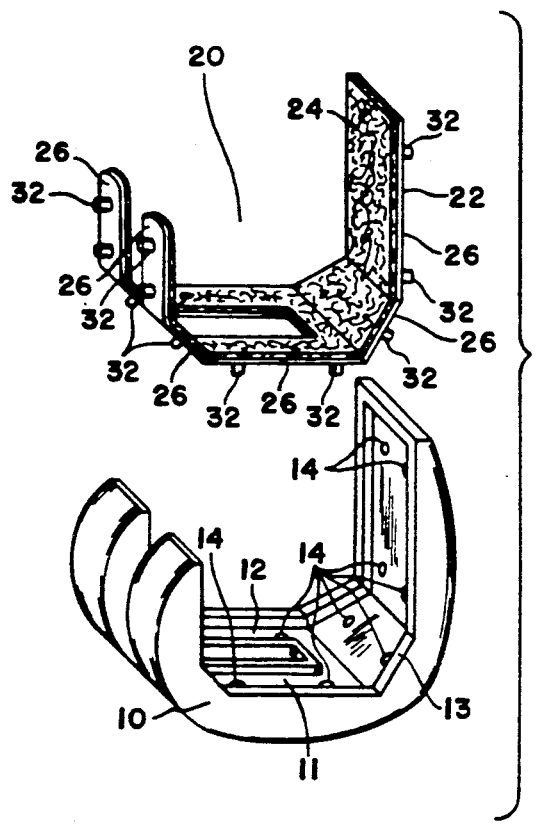
FIG. 2 is an exploded perspective view of the femoral component of FIG. 1.
Figure 3:
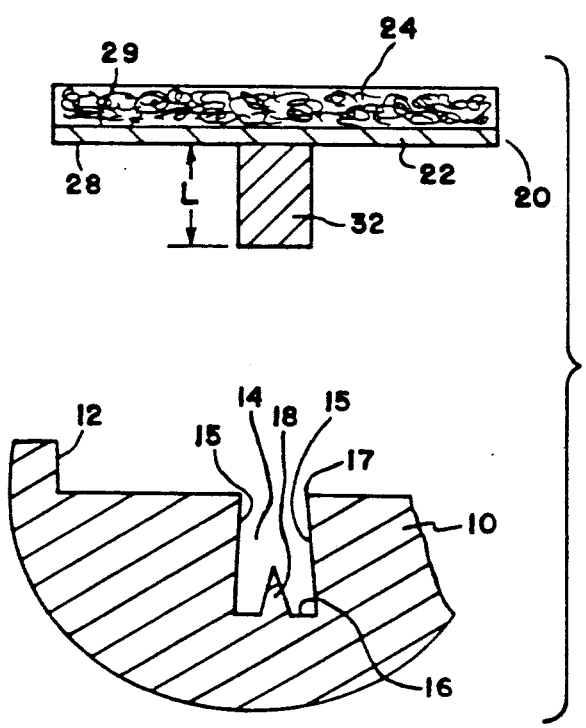
FIG. 3 is an enlarged exploded partial cross-sectional view taken along lines 3—3 of FIG. 1.
Figure 4:
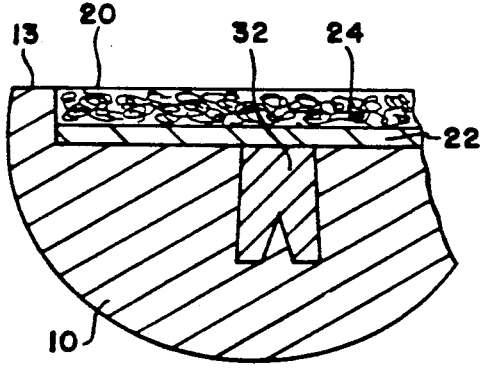
FIG. 4 is an assembled partial cross-sectional view of FIG. 3.
Figure 5:
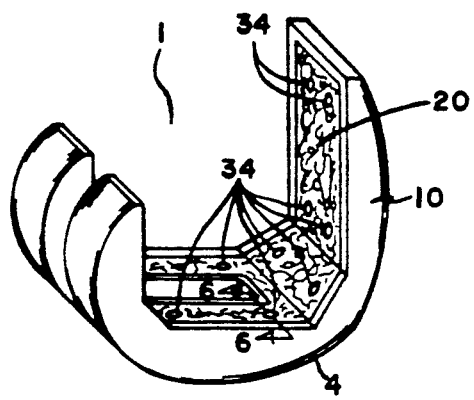
FIG. 5 is a perspective view of an alternate embodiment of a femoral knee implant component in accordance with the present invention.
Figure 7:
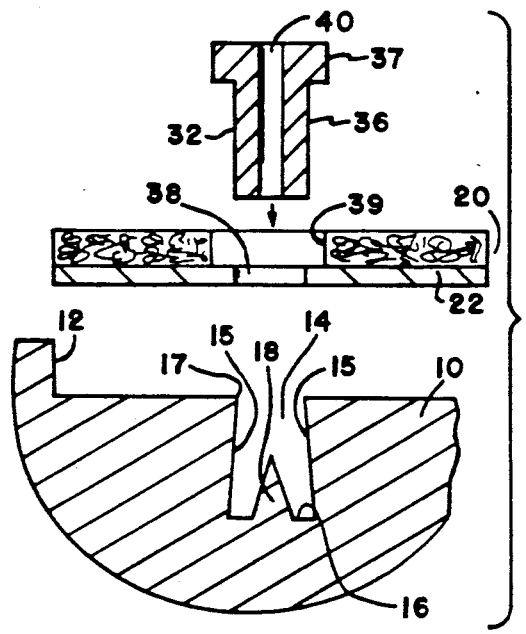
FIG. 7 is an enlarged, exploded partial cross-sectional view of an alternate embodiment taken along lines 6—6 of FIG. 5.
Figure 6:
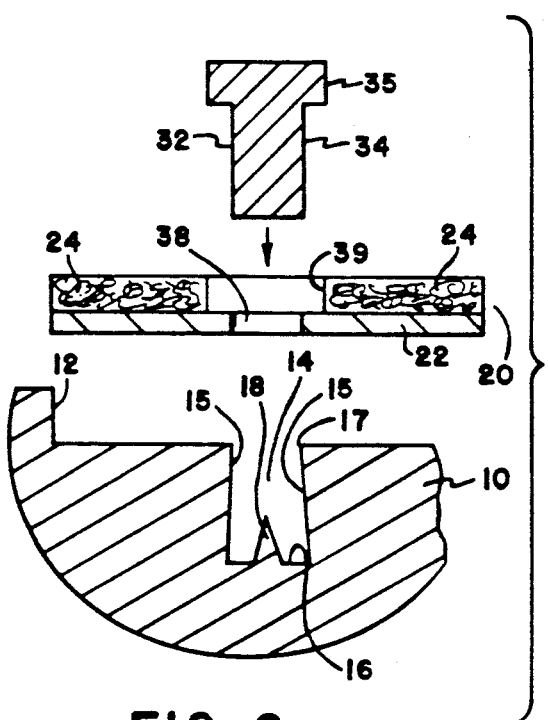
FIG. 6 is an enlarged, exploded partial cross-sectional view taken along lines 6—6 of FIG. 5.
Figure 8:
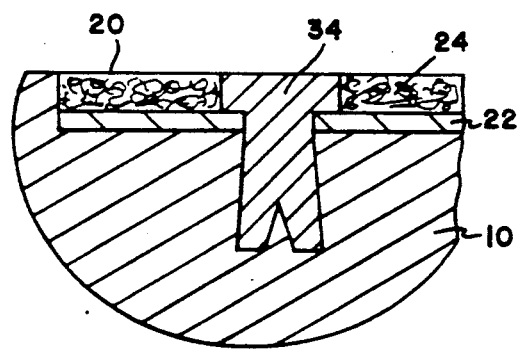
FIG. 8 is an assembled partial cross-sectional view of FIG. 6.
Figure 9:
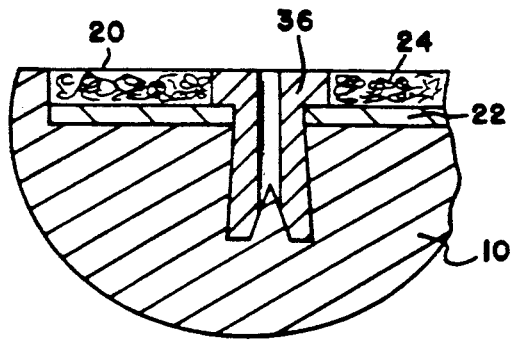
FIG. 9 is an assembled partial cross-sectional view of FIG. 7.

The prosthetic implant 1 of FIGS. 1-4 includes a base portion 10 having a receiving surface 11 and an additional portion 20 which is to be securely attached to the receiving surface 11. The receiving surface 11 includes holes 14 therein with each hole 14 including an opening 17 on the receiving surface 11 and an inner wall 15 with a reverse taper extending therefrom such that the hole 14 widens as it progresses into the implant 1. The additional portion 20 includes a substrate 22 with a first or interfacing surface 28 and a second surface 29, with posts 32 extending from the first surface 28 positioned and adapted to be received in the correspondingly located holes 14. For the femoral implant 1 shown, it is particularly advantageous for the holes 14 to be blind holes, so that the holes do not penetrate the articulating surface 4. Thus, the reverse tapered wall 15 of the blind hole 14 terminates at a bottom surface 16. The hole 14 as shown in FIGS. 3-4 includes a means for spreading the post 32 such that upon insertion of the post 32 into the hole 14, the post is spread out to cause at least a portion of the post 32 to become wider than the opening 17 of the hole 14, thus resisting subsequent separation of the post 32 from the hole 14 to secure the additional portion 20 to the base portion 10 of the implant 1.

The means for spreading the post 32 may be a protruding member 18 which extends from the bottom surface 16. The protruding member 18 may be a pointed cone such that the point of the cone is adapted to penetrate the post 32 upon insertion of the post 32 into the hole 14 thus spreading out the post 32. The post 32 is preferably spread out so that the post 32 securely contacts the reverse tapered walls 15 to resist the subsequent separation of the post 32 from the hole 14.

The additional portion 20 may include a porous surface 24 on the second surface 29 of the substrate 22. The substrate 22 gives support to the porous surface 24. The porous surface 24 may be any suitable porous material, such as a plasma sprayed porous surface or sintered beads or a wire-type mesh or screen material which may be prebonded or secured to the substrate 22 before attachment of the additional portion 20 to the base portion 10. This prebonding of the porous surface 24 to the substrate 22 may be done by diffusion bonding, by sintering, or by other suitable attachment means. A particularly advantageous porous material is the porous fiber metal structure of U.S. Pat. No. 3,906,550 to Rostoker et al. This fiber metal material is preferably diffusion bonded to the substrate 22 to secure it thereto, although other suitable bonding methods could be used.

The receiving surface 11 on the base portion 10 of the implant 1 may be a recessed area 12 which is shaped to accept the additional portion 20. The additional portion 20 may be substantially flush with the rim 13 of the base 10 as shown in FIG. 4, or it may be raised up higher than the rim or be below the rim 13 depending on which is desirable for a given implant design.

The posts 32 may be solid studs which extend from the first surface 28 of the substrate 22 as shown in FIG. 3. The studs may be integrally formed with the substrate or may be secured to the substrate 22 by resistance welding or diffusion bonding or other suitable means. This would preferably be done prior to the attachment of the porous surface 24 to the second surface 29 of the substrate 22. The solid stud is impacted onto the protruding member 18 by appropriate setting tools and fixtures, such as a break press and/or pneumatic and/or hydraulic devices (not shown).

Alternatively, the posts could be separate members such as shown in FIGS. 5-9. The posts could be solid rivet members 34 as in FIGS. 6 and 8 or hollow rivet members 36 with channel 40 therein as in FIGS. 7 and 9. The separate members 34 or 36 each include a post portion 32 extending therefrom. The additional portion 20 in these embodiments includes post holes 38 therethrough adapted to receive the rivet members 34 or 36. The rivets 34 and 36 may include enlarged heads 35 and 37, respectively. Accordingly, the post holes 38 may include an enlarged portion 39 to accept the heads 35 or 37. In these alternate embodiments shown in FIGS. 5-9, the heads 35 or 37 are exposed and substantially flush with the porous surface 24, whereas with the embodiment shown in FIGS. 1-4, the porous surface 24 is not interrupted by the stud heads 35 and 36. Thus, in the embodiment of FIGS. 1-4, the amount of porous surface exposed or available without any interruption is maximized. Maximizing the exposed porous surface 24 is important since porous surfaces are generally used to enhance the ingrowth of bone into the porous surface when implants are installed without any bone cement type of material as is known in the art or is used to enhance the adherence of bone cement to the implant if such cement is used. If the separate rivets 34 or 36 are utilized rather than the extending stud-type post 32, the heads of the rivets 35 and 37 would ideally be sized to maximize the available porous surface area in designs where such a porous surface is utilized.

The hollow rivet 36 may utilize a similarly sized or slightly larger sized protruding member 18 as desired. The protruding member 18 in this embodiment would enter the channel 40 and cause expansion of the internal diameter of the channel 40 via the interference between the size of the protruding member 18 and the diameter of the channel 40 to expand the outside configuration of the hollow rivet 36 against the reverse tapered walls 15 to secure the hollow rivet 36 in the hole 14.

FIG. 12 shows an alternate embodiment of the additional portion 20 of FIG. 3 where the post 32 which extends from surface 28 of the substrate 22 is hollow and includes a channel 40.

A further alternate method of attaching the solid or hollow rivets 34 and 36, respectively, to the substrate 22 is shown in FIGS. 13 and 14. In this method the rivet is precisely positioned in a post hole 38 with enlarged portion 39 to accept heads 35 or 37 in the substrate 22. The porous surface layer (fiber metal pad or beads or other suitable porous material) 24 is positioned over the surface 29 to conceal the heads. The whole additional portion assembly 20 may be diffusion bonded or sintered prior to attachment of this assembly to the receiving surface 11 through the holes 14 of the implant 1. This enables the exposed porous surface 24 to be uninterrupted by the heads 35 or 37 since the rivet heads are concealed by the porous surface.

A further alternate embodiment of the hollow rivet 36 is shown in FIGS. 10-11. In this embodiment, the means for spreading the post is not included in the hole as with the protruding member 18 of the other embodiments. Instead, the spreading means may be provided by a separate tool such as plunger 50 which includes an enlarged tip 51 with a tapered end 52. The diameter "$d_1$" of the enlarged tip 51 of tool 50 is slightly larger than the diameter "$d_2$" of channel 40. The enlarged tip 51 could also be spherically-ended (not shown) in which the diameter of the sphere would be "$d_1$". Any other suitable plunger shape could be utilized. The plunger 50 is forced or impacted into the channel 40 which causes the upper portion of the channel 40 to deform, enlarging it to the "$d_1$" diameter. This causes the outer diameter of the upper portion of the post portion of hollow rivet 36 to spread out or deform and thus contact a portion (contact height "h") of the tapered walls 15. The plunger 50 is then removed. The plunger 50 may be a manual instrument such as shown in FIG. 11 in which a hammer force is applied to the head 54 of the plunger. Alternatively, the plunger 50 may have a controlled force applied to it by an automated machine (not shown) which impacts or forces the plunger into the channel 40 by controlled loads and feed rates. Such a plunger 50 may be constructed of hardened steel or other suitable material, such as carbide.

In any of the above-described embodiments, the additional portion 20 may include an integrally formed, single substantially flat substrate 22. The substrate 22 may be conformed to the desired configuration which as shown in FIG. 2 is a plurality of substantially flat segments 26. The segments 26 may be integrally formed in one sheet or piece or they may be separate sections. The substrate may be a substantially flat plane, a series of substantially flat planes or an otherwise suitably contoured or formed member as desired. If a single segment or separate multiple segments 26 are utilized, each separate segment should include at least one post 32 adapted to be received in a corresponding hole 14. If the substrate 22 is formed of several segments 26 which are integrally formed it may not be necessary to include at least one post 32 extending from each segment. The number of posts 32 utilized would depend on the specific design configuration chosen.

The attachment mechanism of the present invention is particularly suitable for the attachment of two portions having dissimilar bonding capabilities, although it is not limited thereto. Thus, the base portion 10 may be formed of one metallic material while the substrate 22 and porous surface 24 are each formed of a metallic material different from the one used for the base portion 10. For example, the base portion 10 may be formed of a cobalt-chrome material while the substrate 22 and porous surface 24 may be formed of titanium material or alloy. However, it is understood that this attachment mechanism may be utilized with any suitable material or combination of materials.

It is also noted that for certain implants, it may be appropriate for the posts 32 to extend from the base portion 10 with the corresponding holes 14 in the additional portion 20, rather than have the posts 32 extend from the additional portion as described above. This variation is not shown in the FIGS.

The corresponding method of securing the additional portion 20 to the base portion 10 includes providing the base portion 10 with a receiving surface 11 and then forming the holes 14 in the receiving surface 11 having openings 17 on the receiving surface 11 and each hole 14 having an inner wall 15 with a reverse taper extending from the opening 17 such that the hole 14 widens as it progresses into the implant. The substrate 22 is provided with corresponding posts 32 extending from its first surface 28. A means is provided for spreading the posts 32. This means may be provided within the holes 14 as with protruding member 18 or by use of an external tool such as plunger 50 as previously described. Upon insertion of the posts 32 into the corresponding holes 14, the spreading means impacts the post 32 to cause at least a portion of the post 32 to become wider than the opening 17 of the hole 14, thus resisting subsequent separation of the post 32 from the hole 14 to secure the additional portion 20 to the base portion 10 of the implant 1. The additional portion 20 may be provided with a porous surface 24 on the second surface 29 of the additional portion 20 prior to the attachment of the additional portion 20 to the base portion 10. Upon attachment of the additional portion 20 to the base portion 10, and thus upon insertion of the posts 32 into the holes 14, the posts 32 are then spread so that the posts 32 securely contact the reverse tapered walls of the corresponding holes 14 to resist the subsequent separation of the posts 32 from the holes 14.

The base portion 10 is suitably sized and shaped in accordance with the prosthetic implant design desired. For the prosthesis 1 of FIGS. 1-14, the recess 12 may suitably be about 2 mm/0.079 in. deep, although the thickness of the prosthesis varies as the contours of the prosthesis vary.

The substrate 22 may be made of thin sheet metal about 0.6 to 1.0 mm/0.024 to 0.0394 in. thick while the porous surface may be about 1.0 to 2.0 mm/0.0394 to 0.0788 in. thick. The posts 32 may be cylindrical prior to insertion into the hole 14 and substantially truncated cone-shaped after they have been spread out after contact with the spreading means. Accordingly, the holes 14 may have circular openings 17 just slightly larger (about 0.05 mm/0.002 in. larger) than the diameter of the posts 32. The holes 14 widen as they progress into the implant 1 forming a truncated cone-shape. The openings 17 may be about 3.23 mm/0.127 in. in diameter while the posts 32 prior to insertion are about 3.18 mm/0.125 in. in diameter ($d_3$). The portion "L" of the posts 32 which extends from the first surface 28 of the substrate 22 may be about 0.5 mm/0.020 in. or more shorter than the depth of the holes 14 prior to insertion of the post 32 therein. This allows room for the post 32 to extend as well as expand, if needed, as it mechanically deforms upon contact with the spreading means. The holes 14 may have a depth of about 3 to 4 mm/0.118 to 0.158 in. The slope "a" of the reverse tapered walls 15 may be about 2 to 15 degrees. The protruding member 18 may be a cone-shaped protrusion with a base diameter of about 1.9 mm/0.075 in. and a height of about 1.27 to 3.81 mm/0.050 to 0.150 in. However, for the hollow rivet design 36, the protruding member may have similar dimensions or it may be slightly larger if desirable for spreading of the posts 32. The channel 40 in the hollow rivet may be about 1.27 mm/0.050 in. in diameter ($d_2$). In the hollow rivet embodiment where plunger 50 is utilized, rather than a protruding member 18, the plunger 50 may have a diameter ($d_1$) of 1.52 mm/0.060 in. The outer dimensions of the posts 32 after insertion into the holes 14 generally spread out to conform to at least a portion of the shape of the reverse tapered holes 14. In FIG. 11, the contact height "h" between the post portion 32 of hollow rivet 36 and the reverse tapered walls 15 may be about 1.27 to 2.54 mm/0.050 to 0.100 in. The height "h" of the post/implant contact area is preferably maximized to in turn maximize the pull-out force (the force which would be required to start the post sliding out of the hole 14.)

It is noted that other suitable geometries and specific dimensions may be utilized in keeping with the invention. Optimum dimensions will vary with the specific design requirements desired. While this invention has been described in terms of particularly advantageous embodiments, those skilled in the art can appreciate that modifications can be made without departing from the spirit and scope of this invention.

We claim:

1. A prosthetic implant comprising a first base portion including a receiving surface and a second additional portion which is to be securely attached to the receiving surface, and wherein the receiving surface includes a plurality of holes therein, each hole extending into said first base member and terminating at a bottom surface, and each hole comprising a narrow portion and a widened portion, said widened portion being wider than the narrow portion and said widened portion being closer to the bottom surface than the narrow portion, and wherein the additional portion comprises a substrate with a first surface and a second surface with a plurality of corresponding posts extending from the first surface, with each corresponding post adapted to be received in one of the holes on the receiving surface, each hole including a protruding member therein extending from the bottom surface for being urged into each corresponding post such that upon insertion of each corresponding post into each respective hole, each post is spread out to cause at least a portion of the post to spread into the widened portion to become wider than the narrow portion of each respective hole, thus resisting subsequent separation of each corresponding post from each respective hole to secure the second additional portion to the first base portion of the implant, and wherein the additional portion further includes a porous surface on the second surface of the substrate.

2. A prosthetic implant comprising a base portion including a receiving surface and an additional portion which is to be securely attached to the receiving surface, the additional portion including an interfacing surface and a surface opposite the interfacing surface, and wherein one of the two of the receiving surface and the interfacing surface includes a plurality of holes therein and the other of the two surfaces includes a plurality of corresponding posts extending therefrom, the plurality of holes each terminating at a bottom surface, and each hole comprising a narrow portion and a widened portion, said widened portion being wider than the narrow portion and said widened portion being closer to the bottom surface than the narrow portion, each corresponding post adapted to be received in each respective hole, each hole including a protruding member therein extending from the bottom surface for being urged into each corresponding post such that upon insertion of each corresponding post into each respective hole each post is spread out to cause at least a portion of the post to spread into the widened portion to become wider than the narrow portion of each respective hole, thus resisting subsequent separation of each corresponding post from each respective hole to secure the additional portion to the base portion of the implant, and wherein the additional portion further includes a porous surface on the surface opposite the interfacing surface.

3. The prosthetic implant of claim 1 wherein the substrate includes a plurality of corresponding post holes therethrough, and wherein the plurality of posts are adapted to be received in the corresponding post holes and wherein each post includes an enlarged head which is seated in the substrate and wherein the porous surface is adapted to conceal each head when the porous layer is secured to the substrate.

4. The prosthetic implant of claim 1 wherein the base portion is formed of one metallic material and the substrate and porous surface are each formed of a metallic material different from the one metallic material.

5. The prosthetic implant of claim 4 wherein the base portion is formed of a cobalt-chrome material and the substrate and porous surface are each formed of a titanium material or alloy.

6. The prosthetic implant of claim 1 wherein the protruding member is a pointed cone shape such that the point of the cone is adapted to enter the corresponding post upon insertion of the corresponding post into each respective hole and upon impaction of the corresponding post onto the respective protruding member.

7. The prosthetic implant of claim 1 wherein each post is integrally formed with the substrate.

8. The prosthetic implant of claim 1 wherein each post is a solid stud.

9. The prosthetic implant of claim 1 wherein each post is a hollow post.

10. The prosthetic implant of claim 1 wherein the additional portion includes a plurality of corresponding post holes therethrough, and wherein the plurality of posts are adapted to be received in the corresponding post holes.

11. The prosthetic implant of claim 10 wherein each post is a solid post.

12. The prosthetic implant of claim 10 wherein each post includes a channel therein.

13. The prosthetic implant of claim 1 wherein the receiving surface of the base portion is a recess for accepting the additional portion.

14. The prosthetic implant of claim 1 wherein the additional portion is comprised of an integrally formed, single substrate.

15. The prosthetic implant of claim 1 wherein the base portion is formed of one metallic material and the substrate is formed of a different metallic material.

16. A prosthetic implant comprising a first base portion including a receiving surface and a second additional portion which is to be securely attached to the receiving surface, and wherein the receiving surface includes a plurality of holes therein extending into said first base member, each of said holes terminating at a bottom surface, and comprising a narrow portion and a widened portion, said widened portion being wider than the narrow portion and said widened portion being closer to the bottom surface than the narrow portion, and wherein the additional portion comprises a substrate with a first surface and a second surface, and wherein the additional portion comprises multiple separate segments, each segment including at least one post extending from said first surface and wherein the receiving surface of the base portion is comprised of multiple planes having different orientations, such that each plane includes a corresponding hole for each at least one post for insertion of the post therein, the at least one post adapted to be received in said corresponding hole, said corresponding hole including a protruding member therein extending from the bottom surface for being urged into the at least one post such that upon insertion of the at least one post into said corresponding hole, the post is spread out to cause at least a portion of the post to spread into the widened portion to become wider than the narrow portion of said corresponding hole, thus resisting subsequent separation of the at least one post from said corresponding hole to secure the second additional portion to the first base portion of the implant.

17. A prosthetic implant comprising a first base portion including a receiving surface and a second additional portion which is to be securely attached to the receiving surface, and wherein the receiving surface includes at least one hole therein extending into said first base member and terminating at a bottom surface, the at least one hole comprising a narrow portion and a widened portion, said widened portion being wider than the narrow portion and said widened portion being closer to the bottom surface than the narrow portion, and wherein the additional portion comprises a substrate with a first surface and a second surface with at least one post extending from the first surface, the at least one post adapted to be received in the at least one hole, the at least one hole including a protruding member therein extending from the bottom surface for being urged into the at least one post such that upon insertion of the at least one post into the at least one hole, the post is spread out to cause at least a portion of the post to spread into the widened portion to become wider than the narrow portion of the at least one hole, thus resisting subsequent separation of the at least one post from the at least one hole to secure the second additional portion to the first base portion of the implant, wherein the substrate comprises a porous layer with the at least one post extending from the porous layer.

* * * * *